United States Patent [19]
Westerfield et al.

[11] Patent Number: 5,594,546
[45] Date of Patent: Jan. 14, 1997

[54] DIAMOND ANVIL CELL FOR SPECTROSCOPIC INVESTIGATION OF MATERIALS AT HIGH TEMPERATURE, HIGH PRESSURE AND SHEAR

[75] Inventors: Curtis L. Westerfield, Espanola; John S. Morris; Stephen F. Agnew, both of Los Alamos, all of N.M.

[73] Assignee: The Regents of the University of California, Los Alamos, N.M.

[21] Appl. No.: 412,383

[22] Filed: Mar. 28, 1995

[51] Int. Cl.$^6$ .................................................. G01N 21/03
[52] U.S. Cl. ................................. 356/246; 356/70
[58] Field of Search ............................ 356/70, 244, 246

[56] References Cited

U.S. PATENT DOCUMENTS

| | | | |
|---|---|---|---|
| 4,009,962 | 3/1977 | Lauer et al. | 356/70 |
| 4,113,384 | 9/1978 | Lauer et al. | 356/70 |
| 5,200,609 | 4/1993 | Sting et al. | 356/244 |

OTHER PUBLICATIONS

H. A. Spikes, "The Behavior of Lubricants in Contacts: Current Understanding and Future Possibilities," J. Engr. Tribology 208, 3 (1994) (no month).

G. Guangteng et al., "A Study of Parched Lubrication," Wear 153, 91 (1992) (no month).

D. J. Gardiner et al., "Raman Spectra of Lubricants in Elastohydrodynamic Entrapments," Wear 91, 111 (1983) (no month).

N. T. McDevitt et al., "Utilization of Raman Spectroscopy in Tribochemistry Studies," Wear 166, 65 (1993) (no month).

G. J. Exarhos et al., "Real–Time Raman Detection Of Molecular Changes In Ceramics Undergoing Sliding Friction," *Microbeam Analysis*, pp. 125–127 (San Francisco Press, Inc., 1987). (no month).

J. L. Lauer et al., "Analysis of Infrared Spectra of Fluid Films in Simulated EHD Contacts," J. Lubrication Technol., pp. 145 (Apr. 1975).

Leo Merrill et al., "Miniature Diamond Anvil Pressure Cell for Single Crystal X–Ray Diffraction Studies," Rev. Sci. Instrum. 45, 290 (Feb. 1974).

J. L. Lauer et al., "Infrared Emission Spectra of Elastohydrodynamic Contacts," J. Lubrication Technol., p. 230 (Apr. 1976).

V. W. King et al., "Temperature Gradients Through EHD Films and Molecular Alignment Evidenced By Infrared Spectroscopy," J. Lubrication Technol. 103, 65 (Jan. 1981).

G. J. Piermarini et al., "Calibration of the Pressure Dependence of the $R_1$ Ruby Fluorescence Line to 195 kbar," J. Appl. Phys. 46, 2774 (1975).

*Primary Examiner*—Richard A. Rosenberger
*Attorney, Agent, or Firm*—Samuel M. Freund

[57] ABSTRACT

Diamond anvil cell for spectroscopic investigation of materials at high temperature, high pressure and shear. A cell is described which, in combination with Fourier transform IR spectroscopy, permits the spectroscopic investigation of boundary layers under conditions of high temperature, high pressure and shear.

6 Claims, 2 Drawing Sheets

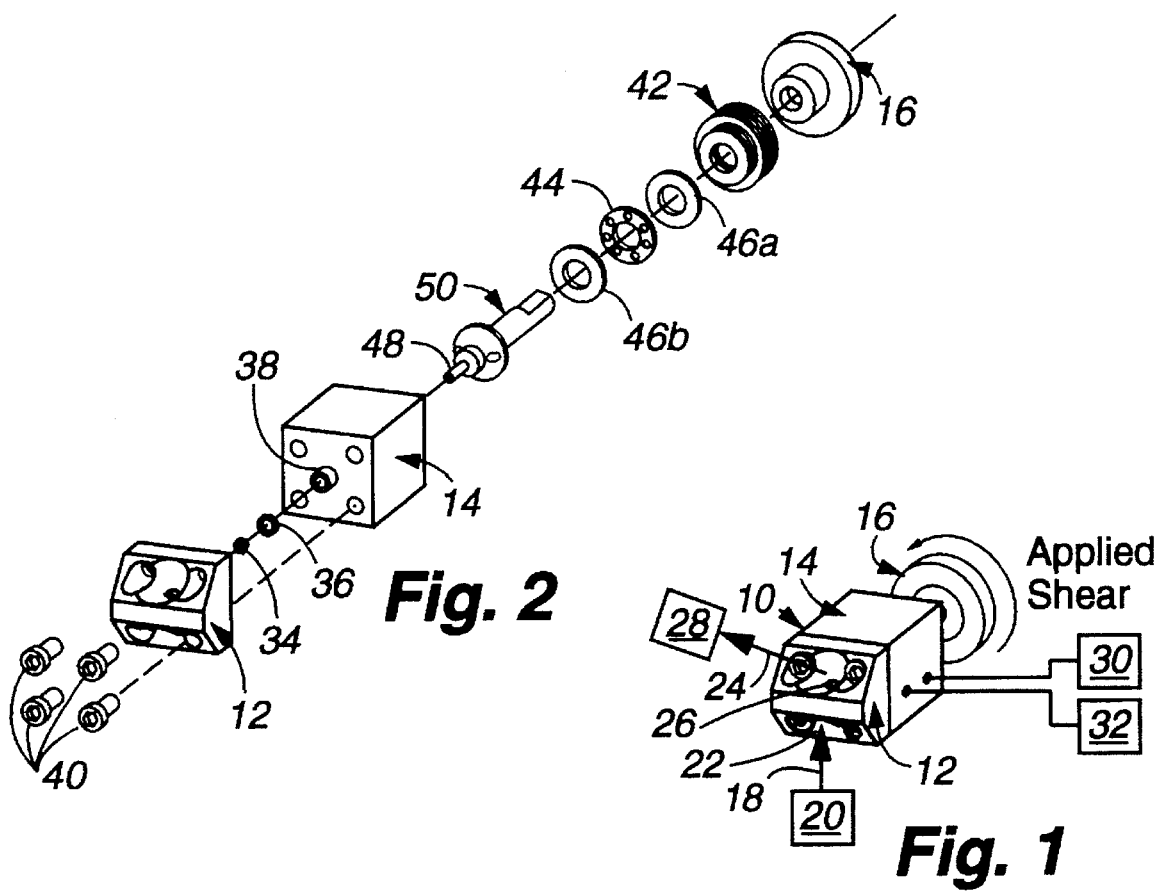
Fig. 2
Fig. 1
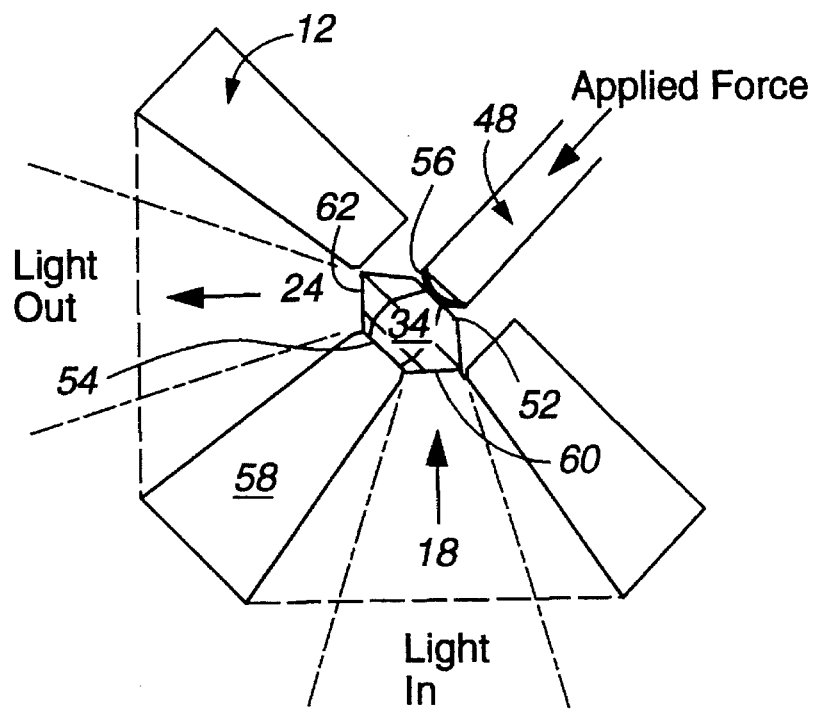
Fig. 3

DIAMOND ANVIL CELL FOR SPECTROSCOPIC INVESTIGATION OF MATERIALS AT HIGH TEMPERATURE, HIGH PRESSURE AND SHEAR

FIELD OF THE INVENTION

The present invention relates generally to the investigation of materials at high temperature and pressure and, more particularly, to the use of spectroscopic techniques to investigate boundary layers under conditions of high temperature, high pressure and shear. The invention was made with government support under Contract No. W-7405-ENG-36 awarded by the U.S. Department of Energy to the Regents of the University of California. The government has certain rights in the invention.

BACKGROUND OF THE INVENTION

Vibrational spectroscopy is considered to be the most powerful technique for probing molecular structure, composition, and phase of materials. Its applicability to the study of boundary layer lubrication and other phenomena where materials contact surfaces at high temperature and pressure in elastohydrodynamic (EHD) contact regions, however, has been greatly reduced due to the inaccessibility of the region of interest to infrared radiation. Thus, only a limited amount of information is available concerning what roles high pressure and temperature play in the formation of boundary layers, and concerning how a given lubrication system will perform in a chosen application. The chemical details of boundary lubrication, which are necessary for the development of new and potentially superior lubricant additives, then, are only sparsely available.

IR and Raman spectroscopy have generally been limited to determining chemical changes in absorbed species before and after wear. See, e.g., "Utilization of Raman Spectroscopy in Tribochemistry Studies," by N. T. McDevitt et al., Wear 166, 65 (1993), and "Real-Time Raman Detection Of Molecular Changes In Ceramics Undergoing Sliding Friction," by G. J. Exarhos and M. S. Donley, *Microbeam Analysis*, pp. 125–127 (San Francisco Press, Inc., 1987).

Diamond anvil cells have long been used to aid in the study of materials under extreme conditions similar to those found in extreme pressure lubrication. Lauer et al., in "Analysis of Infrared Spectra of Fluid Films in Simulated EHD Contacts," J. Lubrication Technology, pp. 145–150 (April 1975), describe the use of interferometric techniques to observe infrared absorption and emission spectra having excellent resolution from small EHD contact regions, in order to determine phase and structural changes in fluids subjected to conditions prevailing in EHD contacts. Contact simulation was believed to be achieved in the cavity of a high-pressure diamond anvil cell. However, the standard Merrill-Bassett type diamond anvil cells employed (See, e.g., "Miniature Diamond Anvil Pressure Cell for Single Crystal X-Ray Diffraction Studies," by Leo Merrill and William Basset, Rev. Sci. Instrum. 45, 290 (1974)) do not provide a metal surface upon which boundary lubrication films can form.

In "Infrared Emission Spectra of Elastohydrodynamic Contacts," by J. L. Lauer and M. E. Peterkin, J. Lubrication Technol., pp. 230–235 (April 1976), and in "Temperature Gradients Through EHD Films and Molecular Alignment Evidenced By Infrared Spectroscopy," by V. W. King and J. L. Lauer, J. Lubrication Technol. 103, 65 (January 1981), the authors describe the observation of infrared emission spectra from thin films of a test fluid located between a diamond disk mounted as a window in a steel plate and a weighted, steel ball which was rotated over the window so as to form a sliding EHD contact region. Some of the radiant energy generated from small areas of this region, both in the fluid and at the boundaries, passes through the diamond window into an infrared interferometer, giving rise to an infrared spectrum. The spectrum may be separated into contributions from the fluid and from the ball surface, making it possible, by appropriate calibrations, to estimate their temperature separately under operating conditions.

Accordingly, it is an object of the present invention to provide a diamond anvil cell which permits the investigation of boundary layer type films under conditions similar to those found in extreme pressure lubrication, and which may be used with spectroscopic techniques including IR absorption, Raman scattering, uv-visible absorption, and fluorescence.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the diamond anvil spectroscopic cell for observation of fluids under high pressure, temperature and shear using electromagnetic radiation having a chosen wavelength and bandwidth, of the present invention includes a diamond having a first flat face, a second, opposing flat face parallel to the first face, a third flat face, and a fourth flat face separated by the first face and disposed at approximately 45° thereto and approximately 90° to each other; means for holding the diamond in a fixed position adapted to permit electromagnetic radiation to enter the third face of the diamond and exit the fourth face and both enter and exit the second face thereof; a metal pin having a rounded end; and means for applying force to the metal pin such that the rounded end thereof is pressed against the second flat face of the diamond, thereby forcing the first face of the diamond against the holding means; whereby a fluid of interest is compressed to a desired pressure between the second face of the diamond and the rounded end of the metal pin, and spectroscopic investigation can be accomplished by directing electromagnetic radiation having a chosen wavelength and bandwidth perpendicularly through the third face of the diamond in such a manner that it exits the second face thereof passing through the liquid under investigation, the radiation being reflected by the rounded end of the pin through the liquid under investigation a second time and reentering the diamond through the second face thereof such that it exits the fourth face into analytic means.

Preferably, means are provided to heat the pin and the diamond.

Benefits and advantages of the present invention include direct, real-time spectroscopic observation of the effects of temperature, pressure and shear on fluids or films which form the interface between hard surfaces.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings:

FIG. 1 is a perspective view of a schematic representation of the diamond anvil spectroscopic cell of the present invention.

FIG. 2 is an exploded schematic representation of the component parts of the diamond anvil spectroscopic cell of the present invention shown in FIG. 1 hereof.

FIG. 3 is an exploded schematic representation of the Type IIa diamond utilized in the diamond anvil spectroscopic cell illustrated in FIGS. 1 and 2 hereof, showing the enlarged facets essential for the effective coupling of electromagnetic radiation into and out of the sample.

DETAILED DESCRIPTION

Figure 4:
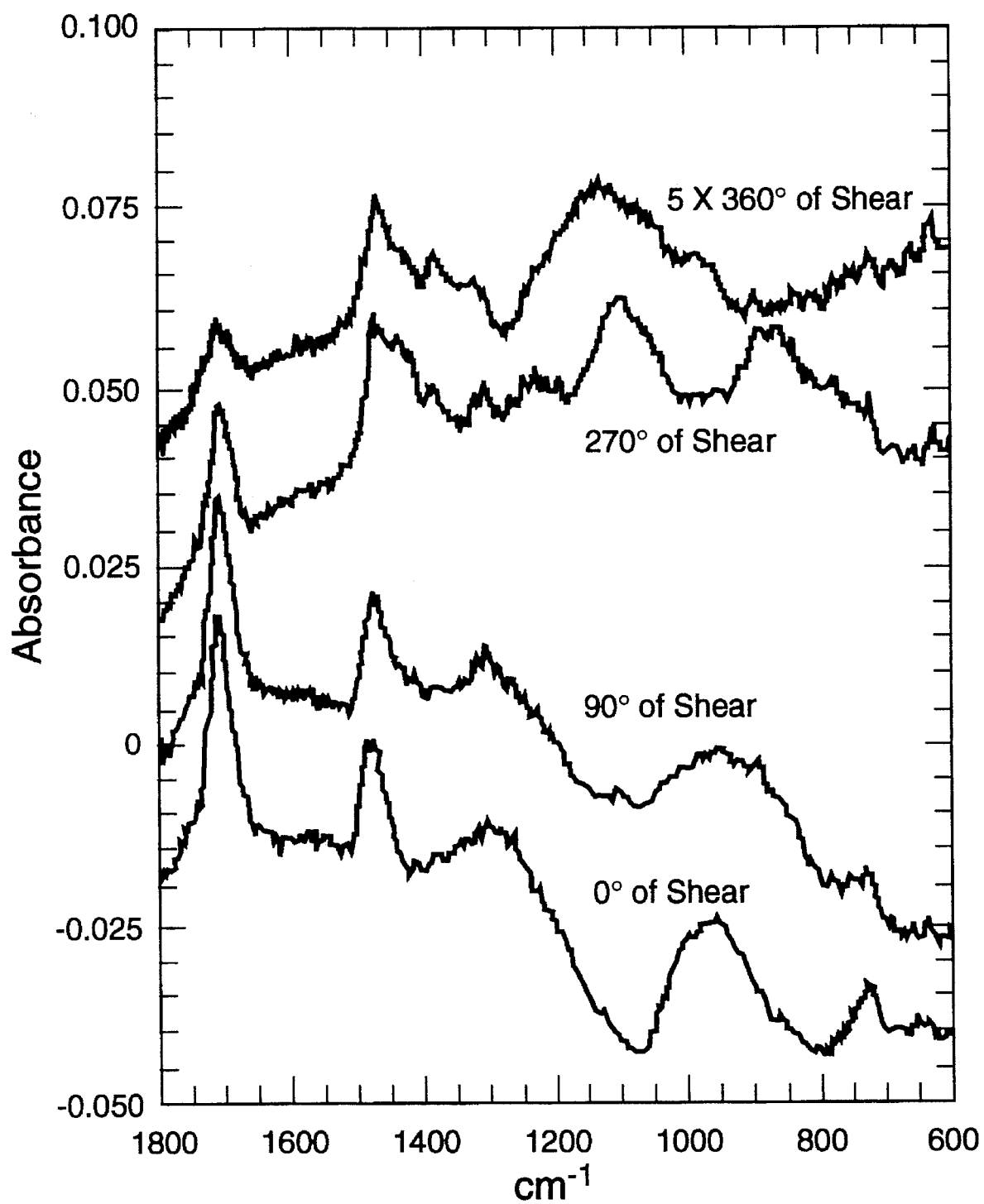
FIG. 4 shows spectra of stearic acid film at a pressure of 3.0 GPa using the present diamond anvil spectroscopic cell at 30° C.

Briefly, the present invention includes a diamond anvil spectroscopic cell which, when combined with the techniques of IR spectroscopy, such as Fourier transform IR (FTIR) spectroscopy, permits the investigation of boundary-layer phenomena at hard surfaces at high temperature, pressure and shear.

Reference will now be made in detail to the present preferred embodiment of the invention, an example of which is illustrated in the accompanying drawings. In the Figures, similar or identical structure is designated by identical callouts. FIG. 1 shows a perspective view of a schematic representation of the assembled diamond anvil spectroscopic cell, 10, of the present invention. Diamond holder, 12, is shown attached to block member, 14. Knob, 16, is part of means for applying shear forces between a pin (not shown) and the surface of a diamond (not shown), between which the fluid under investigation is located. Diamond holder, 12, is adapted to receive probe electromagnetic radiation, 18, from source 20, having a chosen wavelength and bandwidth, through inlet hole 22, such that radiation 18 is incident on the diamond. After interrogating the fluid, exiting electromagnetic radiation, 24, emerges through hole 26 in diamond holder 12, and is detected and analyzed by analyzer 28. Block member 14 and diamond holder 12 may be heated by heater, 30, to a desired temperature, which is measured by temperature measuring apparatus, 32, having a thermocouple located near to the diamond (not shown).

FIG. 2 illustrates an exploded schematic representation of the principal components of the assembled apparatus shown in FIG. 1. Diamond, 34, is a Type IIa diamond having low nitrogen content in order to reduce its absorption in the infrared. A tellurium copper gasket, 36, holds diamond 34 in diamond holder 12. Hollow cylindrical protrusion, 38, in block member 14, initially compresses gasket 36 against diamond 34 in a recess in diamond holder 12 adapted for this purpose, when the two units are bolted together using screws, 40. The diamond is then permanently secured and indexed. Load screw, 42, and thrust bearing, 44, which is located between hardened races, 46a and 46b, provide a chosen force in the axial direction to pin, 48 (A-2 steel, 1.5 mm dia.), through rotator shaft, 50. The face of pin 48 is rounded (radius of curvature, 0.045 in.) at the tip to minimize cupping of its surface under load and to maximize the contact of the tip with the diamond. Load screw 42 screws into block member 14 by means of a matching threaded portion therein (not shown). Knob 16 is used to provide shear forces to the fluid located between pin 48 and diamond 34. Pressures between the pin and the diamond are determined by observing pressure-induced shifts in the ruby fluorescence spectrum. See, e.g., G. J. Piermarini, S. Block, J. D. Barnett and R. A. Forman, "Calibration of the Pressure Dependence of the $R_1$ Ruby Fluorescence Line to 195 kbar," J. Appl. Phys. 46, 2774 (1975).

FIG. 3 shows an exploded schematic representation of diamond 34 situated in diamond holder 12. Diamond 34 has two opposing approximately parallel flat faces, 52 and 54. Face 52 is disposed approximately perpendicular to the axis of pin 48. The fluid under investigation, 56, is located in between pin 48 and face 52. Face 54 is forced against portion 58 of diamond holder 12 by both gasket 36 and the action of pin 48 on face 52. The planes of faces 60 and 62 of diamond 34 are each located at approximately 45° to the plane of face 54, and approximately 90° to each other. This configuration permits incident electromagnetic radiation 18 to pass through face 60, enter diamond 34, exit through face 52, pass through fluid 56, reflect from the face of pin 48, pass through fluid 56 once again, reenter diamond 34 through face 52, and exit face 62 as output beam 24 carrying spectroscopic information concerning fluid 56 to analyzer 28. Thus the electromagnetic radiation probes the contact surface between the diamond and pin 48 while a load and/or torque is applied to pin 48.

IR spectra were recorded with a FTIR spectrometer. Minor modifications in the spectrometer allowed the use of an IR microscope with a 32× objective. Further modifications allowed the microscope to be used in a right-angle reflection geometry.

Spectra taken using the present diamond anvil spectroscopic cell are shown in FIG. 4. The samples were prepared by soaking the pin for 1 hour in a 5% w/w hexane solution of stearic acid. The pin was then removed from the solution and allowed to dry in the air. Approximate film thicknesses were determined by first determining the absorptivity of the carbonyl in mineral oil solutions of known concentration. The thickness of stearic acid films prepared in this way was highly variable (0.1–1.0 μm). The resulting films proved to be temperature insensitive up to 200° C. Thick (about 1.0 μm) films were also found to be insensitive to shear, but thin films proved to be susceptible to shear-induced chemistry. FIG. 4 shows FTIR spectra of an approximately 0.1 μm stearic acid layer at 30° C. and 3.0 GPa before and after the application of shear. It may be observed that shear causes the carbonyl peak at 1708 $cm^{-1}$ to decrease in intensity while causing the C-H deformation mode initially at 1475 $cm^{-1}$ to broaden and to red shift to 1466 $cm^{-1}$. In addition several new broad peaks are observed which have been tentatively assigned to be the products resulting from the anaerobic reduction of carbon caused by the highly reducing metal surface exposed by shear. The spectra clearly indicate that the present spectroscopic cell can be used to observe boundary-layer type films under conditions of high temperature and pressure, and that shear-induced chemistry can be observed.

The foregoing description of the invention has been presented for purposes of illustration and description and is not intended to be exhaustive or to limit the invention to the precise form disclosed, and obviously many modifications and variations are possible in light of the above teaching. For example, it would be apparent to one skilled in the spectroscopic arts, after studying the present disclosure, that spectroscopic wavelengths other than those in the infrared region of the electromagnetic spectrum may be employed.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A diamond anvil spectroscopic cell for observation of surface films under high pressure, temperature and shear using electromagnetic radiation having a chosen wavelength and bandwidth, which comprises in combination:

a. a diamond having a first flat face, a second, opposing flat face approximately parallel to the first face, a third flat face, and a fourth flat face separated by the first face and disposed at approximately 45° thereto and approximately 90° to each other;

b. means for holding said diamond in a fixed position, said means being adapted to permit electromagnetic radiation to enter the third face of said diamond and exit the fourth face and both enter and exit the second face thereof;

c. a hard pin having a rounded end; and d. means for applying force to said metal pin such that the rounded end thereof is pressed against the second flat face of said diamond, thereby forcing the first face of said diamond against said means for holding said diamond; whereby a fluid of interest is compressed to a desired pressure between the second face of said diamond and the rounded end of said metal pin, and spectroscopic investigation can be accomplished by directing electromagnetic radiation having a chosen wavelength and bandwidth perpendicularly through the third face of said diamond and out of the second face thereof and into the liquid under investigation, where it is reflected by the rounded end of said pin and passes through the liquid under investigation a second time, reentering said diamond through the second face thereof and exits the fourth face of said diamond for analysis.

2. The spectroscopic cell as described in claim 1, further comprising means for heating said diamond and said pin to a desired temperature.

3. The spectroscopic cell as described in claim 2, wherein said diamond is a Type IIa diamond having low infrared radiation absorption.

4. The spectroscopic cell as described in claim 1, wherein the wavelength of the electromagnetic radiation is chosen to be in the infrared region of the electromagnetic spectrum.

5. The spectroscopic cell as described in claim 1, wherein said hard pin is fabricated from steel.

6. The spectroscopic cell as described in claim 1, wherein said means for applying force to said pin includes a screw mechanism.

* * * * *